United States Patent [19]

Kopolow

[11] Patent Number: 5,779,944
[45] Date of Patent: Jul. 14, 1998

[54] WATER DISPERSIBLE PERFLUOROETHER POLYMER ENCAPSULATES

[75] Inventor: Stephen L. Kopolow, Plainsboro, N.J.

[73] Assignee: ISP Investments Inc., Wilmington, Del.

[21] Appl. No.: 948,914

[22] Filed: Oct. 10, 1997

[51] Int. Cl.⁶ .............................. A61K 7/00; A61K 9/50
[52] U.S. Cl. ............... 264/4.7; 428/402.22; 427/213.34
[58] Field of Search .............. 264/4, 4.7; 428/402.22; 427/213.34

[56] References Cited

U.S. PATENT DOCUMENTS

| | | |
|---|---|---|
| 2,969,330 | 1/1961 | Brynko . |
| 2,969,331 | 1/1961 | Brynko et al. . |
| 3,242,218 | 3/1966 | Miller . |
| 3,665,041 | 5/1972 | Sianesi et al. . |
| 3,715,378 | 2/1973 | Sianesi et al. . |
| 4,155,741 | 5/1979 | Scher et al. ............... 71/65 |
| 4,523,039 | 6/1985 | Lagow et al. ............ 568/615 |
| 4,741,872 | 5/1988 | De Luca et al. ........... 264/4.7 |
| 4,803,067 | 2/1989 | Brunetta et al. ........... 424/63 |
| 4,959,171 | 9/1990 | Pantini et al. ............ 252/174 |
| 5,073,296 | 12/1991 | Kopolow et al. ........... 252/312 |
| 5,093,023 | 3/1992 | Pantini et al. ......... 252/174.23 |
| 5,252,325 | 10/1993 | Bires et al. ............... 424/71 |
| 5,401,634 | 3/1995 | Milbrath .................. 435/6 |
| 5,455,048 | 10/1995 | Lahmani et al. ........... 424/490 |
| 5,459,165 | 10/1995 | Bollens et al. ............ 514/768 |
| 5,607,979 | 3/1997 | McCreery ................ 514/759 |
| 5,705,165 | 1/1998 | Bollens et al. ............ 424/401 |
| 5,705,179 | 1/1998 | Fulton, Jr. ............... 424/423 |
| 5,711,951 | 1/1998 | Kopolow ................. 424/401 |

OTHER PUBLICATIONS

CA abstract 123:34712, Abstracting JP06304469., Nov. 1994.
CA abstract 87:119098, Abstracting DE2602176., Aug. 1977.
WPIDS An 97–060809, Abstracting JP08309903 A., Nov. 1996.

*Primary Examiner*—Jeffrey Mullis
*Attorney, Agent, or Firm*—Marilyn J. Maue; William J. Davis; Walter Katz

[57] ABSTRACT

This invention relates to a water insoluble encapsulate comprising a water insoluble polymer of a perfluoroether containing perfluorinated isopropyloxy units and having a number average molecular weight of between about 450 and about 15,000 which polymer is encapsulated in a water soluble, non-halogenated polymer and to the stable, homogeneous, aqueous compositions of the encapsulated perfluoroether polymer in various formulations of cosmetically, pharmaceutically and agrochemically active substances.

23 Claims, No Drawings

WATER DISPERSIBLE PERFLUOROETHER POLYMER ENCAPSULATES

BACKGROUND OF THE INVENTION

The important properties contributed by perfluoroether polymer oils such as high lubricity, epidermal substantivity and emolliancy make them highly desirable as active components in many formulations for the treatment of animals and plants, particularly in hair and skin formulations for superior conditioning and mollescent affects. However, the use of these perfluorinated compounds has been limited because of their extreme insolubility in aqueous media. Attempts to improve their stability in water, have proved unsatisfactory since it has been necessary to include one or more surfactants in their formulation with aqueous cosmetic or pharmaceutical compositions. This solution to the problem has not met with wide acceptance since the inclusion of extraneous additives not only increases the cost of the product but also dilutes the effectiveness of the polyperfluoroether component thus lowering the quality of the composition. It is further noted that, even in the presence of surfactant, the stability in aqueous solution is not improved to a marked extent.

Prior attempts to improve stability of water insoluble, non-halogenated or less insoluble monochlorinated oils in water involve the formation of oil macroscopic capsules by in situ polymerization with a water soluble component. For example, Brynko, in U.S. Pat. Nos. 2,969,330 and 2,969,331, described the preparation of pressure-rupturable capsules of a chlorodiphenyl oil in water by dissolving styrene, an acrylate or vinyl acetate monomer in the oil, dispersing the monomer-containing oil in water with the aid of an emulsifier to form droplets and polymerizing the monomer to form a shell of polymer around each oil droplet.

Berg, in J. Microencapsulation (1989) 6, No. 3, 327–337, also described a process for the microencapsulation of emulsified oil droplets by in situ polymerization. However, the process was limited to the use of methyl methacrylate, an oil soluble monomer, to form a polymer shell around emulsified oil droplets of decane and hexadecane.

De Luca, in U.S. Pat. No. 4,741,872, described the preparation of biodegradable microspheres having a three-dimensional network in which biologically active macromolecular agents were physically entrapped therein. The method involved emulsifying a vinyl derivative of a biodegradable hydrophilic polymer, a water-soluble monovinyl monomer, and a biologically active macromolecular agent, in water, and copolymerizing the vinyl compounds.

U.S. Pat. No. 4,155,741 utilizes inorganic chlorides with a sequestering agent to stabilize aqueous suspensions of encapsulated polymers. However, these formulations, like those used before, require extraneous additives to achieve stability and thus weakens the strength of the active component.

Other experimenters have been successful in forming microdroplets of non-halogenated oils for stabilization using in situ polymerization of a water soluble vinyl monomer. Such methods are disclosed in U.S. Pat. Nos. 5,073,296 and 5,252,325 wherein a silicone oil is encapsulated in water soluble vinyl pyrrolidone polymer.

However, the above products and processes do not relate to the highly insoluble perfluorinated polymeric compounds or unique chemical properties imparted by fluorinated ether polymers. Similarly, the above references fail to suggest means for maintaining polymers of such perfluorinated ethers in stable condition in aqueous formulations for any extended period of time.

Accordingly, it is an object of the present invention to overcome the above problems and to provide a water insoluble polyperfluorinated ether oil in a homogeneous durably stable, water dispersible state for incorporation into an aqueous formulation.

Another object of the invention is to provide a stable aqueous composition which includes discrete microdroplets of a polyperfluorinated ether encapsulated in a water-soluble polymer in the absence of a surfactant.

Still another object of the invention is to provide the above perfluorinated product by commercially feasible and economical process.

Still another object is to provide a superior conditioning and emolliating agent for use in aqueous cosmetic, pharmaceutical or agrochemical formulations.

These and other objects and features of the invention will become apparent from the following description and disclosure.

ABBREVIATIONS AND DEFINITIONS USED HEREIN

Oil—A compound which is water-insoluble at room temperature and has an oily consistency.
VP—N-vinyl pyrrolidone.
VCL—N-vinylcaprolactam.
PPFE—polyperfluoroether.
TBP—tertiary-butyl peroctate.
TBPP—tertiary-butylperoxy pivalate.
Cosmetically-active oil or Pharmaceutically-active oil is an oil which imparts a desirable conditioning property to a cosmetic or pharmaceutical formulation.
Brookfield Viscosity is the viscosity in cps of the stabilized oil in water product as measured using a RVT spindle #5 at 5 rpm.

THE INVENTION

In accordance with the present invention there is provided water soluble and water dispersible compositions comprising microdroplets of a water-insoluble poly(perfluoroether) containing a perfluoro isopropyl unit and having a molecular weight of between about 450 and about 15,000, preferably between about 1,200 and about 8,000, which polymer is encapsulated in a water soluble, non-halogenated polymer of a cyclic N-vinyl lactam having from 4 to 6 carbon atoms in the heterocyclic ring.

The polyperfluoroethers of the invention are oils and, of these, the perfluorinated isopropyl ether polymer, e.g. FLUORTRESS®, supplied by duPont, having the formula

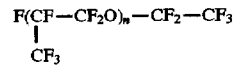

where n has a number average of 4 to 15 and the perfluorinated methyl isopropyl polyoxymethyl ether polymer, e.g. FOMBLIN®, supplied by Montefluids, having the formula

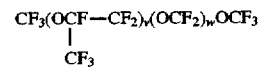

wherein the sum of v+w is a number average of 4 to 20 are preferred species.

As the water insoluble component of the present encapsulate, the perfluorinated ether polymer can be mixed with another cosmetically active oil, e.g. a silicone oil of the type such as disclosed in copending U.S. patent application Ser. No. 08/596,896, now U.S. Pat. No. 5,711,951 filed Mar. 13, 1996 the disclosure of which is incorporated herein by reference. When such mixtures form the water insoluble component employed herein, the perfluorinated oil is present in an effective lubricating or stabilizing amount, which beneficially can be an amount as low as 10 wt. % of the oil mixture.

The N-vinyl lactam encapsulating polymers of this invention include the vinyl lactam homopolymers and vinyl lactam interpolymers of N-vinyl pyrrolidone and N-vinyl caprolactam as well as their $C_1$ to $C_4$ alkyl ring-substituted derivatives and the copolymers of these lactam monomers with water soluble or water miscible comonomers of alkylaminoalkyl methacrylates such as dimethylaminopropyl methacrylate, dimethylaminoethyl methacrylate, methacrylamidopropyltrimethylamino acrylamide, neutralized acrylic acid, and the like. Where lactam copolymers are employed to coat the PPFE droplets, the lactam moiety is at least 60 wt. % of the copolymer composition.

The encapsulates of the present invention can be prepared by adding the perfluorinated oil, or oil mixture, to water under agitation sufficient to form a fine dispersion of discrete oil microdroplets in the aqueous medium and continuing agitation until the dispersion is stable against phase separation for 5 to 15 minutes. Thereafter, a water-soluble vinyl monomer, or a mixture of monomers, corresponding to the aforementioned polymers is added along with an appropriate free radical polymerization initiator. Suitable free radical initiators are the conventional peroxide types such as t-butyl peroctate, e.g. TRIGONOX® 21, t-butylperoxy pivalate, e.g. LUPERSOL 11, lauryl peroxide, and the like. Of these, the initiators which are soluble in oil are preferred. The resulting aqueous mixture containing monomer, initiator and water insoluble oil is heated and maintained at a temperature between about 50° and about 90° C., preferably between about 75° and about 87° C. until less than 1 wt. % monomer remains.

As the polymerization proceeds, the dispersed oil droplets become opaque which indicates completion of encapsulation reaction. Generally the polymerization is carried out over a period of from 2 to 20 hours, preferably from 4 to 10 hours to reduce the monomer to an acceptable level.

The production of stable, discrete microdroplets of the polyperfluoroether oil in the resulting aqueous polymer mixture can be controlled by regulating the viscosity of the aqueous medium. For example, the viscosity of the medium can be raised by increasing the relative amount of vinyl monomer to oil in the initial reaction mixture. Although a monomer/oil mixture of from 95/5 to 5/95 can be employed, the 95/5 to 50/50 mixture is somewhat tacky; whereas a mixture of 5/95 to about 45/65 has much less tack but the viscosity is such that the mixture may tend to form a separate layer of discrete oil droplets. In such cases the stability and viscosity can be increased without additional tack by adding a thickening agent. Suitable thickening agents include hydroxyethyl cellulose, hydroxypropyl cellulose, carboxymethyl cellulose, guar gum, a silicate, decadiene crosslinked maleic anhydride/methyl vinyl ether copolymer, e.g. STABILEZE® QM, crosslinked acrylic acid/acrylate copolymer, e.g. CARBAPOL®, a clay, e.g. bentonite, colloidal alumina, gum arabic, agar, tragacanth, a high molecular weight polyethylene oxide, e.g. POLYOX, polyacrylamide, e.g. SEPIGEL®, a $C_{13}$ to $C_{14}$ isoparaffin and Laureth-7, a polyglyceryl methacrylate and propylene glycol, e.g. Lubrajel®, the hydrolyzed form of a diene crosslinked maleic anhydride/methyl vinyl ether, e.g. GANTREZ® XL-80W or STABILEZE® XL-80W and the like.

The bulk viscosity required to maintain the discrete microdroplets uniformly distributed throughout the mixture is between about 8,000 and about 100,000 cps, preferably between about 10,000 and 70,000 cps and most preferably between about 20,000 and about 50,000 cps. Generally between about 0.2 and about 2 wt. %, preferably between about 0.3 and about 0.8 wt. % thickener, based on total aqueous composition is employed.

A broad range ratio of vinyl monomer to perfluoroether oil can be employed in the polymerization reaction, e.g. a 95:5 to 5:95 mixture, but is preferably a mixture within the range of from 50/50 to 5/95.

The stabilized product is recovered in aqueous solution wherein the concentration of solids is between about 5 and about 50 wt. %, preferably between about 10 and about 30 wt. %.

In general, the concentration of polyperfluoroether-containing encapsulate incorporated into a standard personal care or pharmaceutical or agrochemical formulation can vary between about 1 and about 15 wt. %, depending upon the added lubricity desired by the formulator.

Some examples of suitable personal care formulations include sun tanning lotions, skin conditioners, shampoos, hair conditioners, hair coloring and bleaching agents, skin bleaching compositions, body lotions, etc. Representative pharmaceutical formulations include topical skin lotions designed to treat acne and other skin disorders. The present products are also useful in agricultural chemical formulations applied as a spray to ornamental plants, crops and weeds where it is desirable to extend the retention of the active chemical on the plant and inhibit leaching into ground water.

The following are representative formulations suitable for incorporating an aqueous solution of the present product, e.g. an aqueous solution of 15% solids containing FLUROTRESS M-550 or FOMBLIN encapsulated in water soluble polyvinyl pyrrolidone and containing 0.2 wt. % STABILEZE® QM thickener. The addition of the present product is made under ambient conditions with constant agitation until a homogeneous mixture is obtained.

| INGREDIENT | |
|---|---|
| FACE LOTION | wt. % |
| deionized water | 78.80 |
| disodium ethylenediamine tetraacetic acid | 0.05 |
| stearic acid | 1.50 |
| cetearyl alcohol | 0.25 |
| Escalol 557 (a) | 7.50 |
| Ceraphyl 368 (b) | 5.00 |
| Vitamin E Acetate | 0.10 |
| Ceraphyl GAD (c) | 1.00 |
| Vitamin A Palmitate | 0.10 |
| Cerasynt 945 (d) | 1.00 |
| triethanolamine (99%) | 0.50 |
| Germaben II (e) | 1.00 |
| Product of the invention | 3.25 |
| TOTAL | 100.00 |
| HAIR CONDITIONER | |
| deionized water | 87.0 |
| cosmedia guar gum C261 | 0.50 |
| propylene glycol | 1.00 |
| cetearyl alcohol | 2.00 |
| MYRJ 52S (f) | 0.50 |
| Incroquat TMS (g) | 3.00 |

-continued

| INGREDIENT | |
|---|---|
| Germaben II | 1.8 |
| citric acid (20% solids, pH 4.0–4.5) | 0.2 |
| Product of the Invention (Aq. Soln.) | 4.0 |
| TOTAL | 100.00 |

SUNSCREEN

| Phase I | % w/w |
|---|---|
| isopropyl myristate | 7.0 |
| octyl dimethyl PABA | 8.0 |
| octyl methoxy cinnamate | 7.5 |
| benzophenone-3 | 5.0 |
| methyl anthranilate | 5.0 |
| stearic acid | 3.0 |
| glyceryl monostearate | 4.0 |
| cetyl alcohol | 1.0 |
| PEG-40 stearate | 1.5 |
| Phase II | |
| Distilled Water | 42.45 |
| Xanthan | 0.3 |
| product of the invention | 3.0 |
| DEA-cetyl phosphate | 8.0 |
| preservative | QS |
| glycerine | 3.5 |
| fragrance | 0.25 |

WOUND DRESSING COMPOSITION

| | |
|---|---|
| PVP/I | 10.0 |
| PEG | 0.5 |
| Ethanol | 40.0 |
| Deionized H$_2$O | 44.5 |
| Product of the Invention | 5.0 |
| | 100.0 |

(a) octyl-p-methoxy cinnamate
(b) 2-ethylhexyl palmitate
(c) maleated soybean oil
(d) glyceryl monostearate and polyoxyethylene lauryl ether
(e) methyl parabenpropyl paraben diazolidinyl urea Having generally described the invention, reference is now had to the following examples which illustrate preferred embodiments but which are not to be construed as limiting to the scope of the invention more broadly set forth in the appended claims.

EXAMPLE 1

Into a 500 ml glass kettle fitted with a Teflon turbine agitator, a nitrogen inlet, and a thermocouple with controller was added 233.66 g of deionized water and 56 g FOMBLIN. The reaction mixture was agitated to disperse the FOMBLIN into fine droplets and simultaneously purged with nitrogen to remove oxygen. The reaction mixture was then heated to 85° C. and 14 g N-vinyl pyrrolidone (nitrogen purged) was added. Over 4 hours at 85° C., four equal amounts of TRIGANOX 21 initiator (total 0.25 g) were added. After 30 minutes from the first addition of initiator, the reaction mixture began to opacify indicating that the encapsulation had started. Two hours after the final addition of the initiator, the level of residual VP was found to be below 500 ppm and the reaction mixture was thickened as described below. In cases where the residual VP is above 500 ppm, it is recommended that a further addition of TRIGANX 21 or other initiator be employed and the residual VP level rechecked after two hours. In any case, the residual VP should not exceed 1000 ppm.

The above reaction mixture (<500 VP) was cooled to 50° C. and stabilizer and preservative added and dissolved therein. Then 2.8 g of a 10% sodium hydroxide solution was added under agitation for 15 minutes; whereupon 26.25 g of SABILEZE® XL-80W* was added to thicken the reaction mixture. After one hour, the mixture was found to be stable and was transferred to a product recovery container. The bulk viscosity of the 20% product was 45,000 cps and the encapsulate size was less than 500 microns.

EXAMPLE 2

Into a 500 ml glass kettle fitted with a Teflon turbine agitator, a nitrogen inlet, and a thermocouple with controller was added 209.58 g of deionized water and 56 g FLUROTRESS M-550. The reaction mixture was agitated to disperse the FLUROTRESS into fine droplets and simultaneously purged with nitrogen to remove oxygen. The reaction mixture was then heated to 85° C. and 14 g N-vinyl pyrrolidone (nitrogen purged) was added. Over 4 hours at 85° C., four equal amounts of TRIGANOX 21 initiator (total 0.75 g) were added. After 30 minutes from the first addition of initiator, the reaction mixture began to opacify indicating that the encapsulation had started. Two hours after the final addition of the initiator, the level of residual VP was checked and found to be below 400 ppm. The reaction mixture was then cooled to 50° C. and stabilizer and preservative added and dissolved therein. Then 5.67 g of a 10% sodium hydroxide solution was added. After 15 minutes under agitation, 52.5 g of SABILEZE® XL-80W* was added to thicken the mixture and, after one hour, the mixture was stable and was transferred to a product recovery container. The bulk viscosity of the 30% product was 14,000 cps and the encapsulate size was less than 500 microns.

EXAMPLE 3

Into a 500 ml glass kettle fitted with a Teflon turbine agitator, a nitrogen inlet, and a thermocouple with controller was added 238.66 g of deionized water and 42 g FLUROTRESS M-550. The reaction mixture was agitated to disperse the FLUROTRESS into fine droplets and simultaneously purged with nitrogen to remove oxygen. The reaction mixture was then heated to 85° C. and 28 g N-vinyl pyrrolidone (nitrogen purged) was added. Over 4 hours at 85° C., four equal amounts of TRIGANOX 21 initiator (total 0.75 g) were added. After 30 minutes from the first addition of initiator, the reaction mixture began to opacify indicating that the encapsulation had started. Two hours after the final addition of the initiator, the level of residual VP was checked and found to be below 500 ppm. The reaction mixture was then cooled to 50° C. and stabilizer and preservative added and dissolved therein. Then 5.67 g of a 10% sodium hydroxide solution was added. After 15 minutes under agitation, 52.5 g of SABILEZE® L-80W* was added to thicken the mixture and, after one hour, the mixture remained stable and was transferred to a product recovery container. The bulk viscosity of the 20% product was 48,000 cps and the encapsulate size was less than 200 microns.

EXAMPLE 4

Into a 500 ml glass kettle fitted with a Teflon turbine agitator, a nitrogen inlet, and a thermocouple with controller was added 209.58 g of deionized water and 49 g FLUROTRESS M-550. The reaction mixture was agitated to disperse the FLUROTRESS into fine droplets and simultaneously purged with nitrogen to remove oxygen. The reaction mixture was then heated to 85° C. and 21 g N-vinyl pyrrolidone (nitrogen purged) was added. Over 4 hours at 85° C., four equal amounts of TRIGANOX 21 initiator (total 0.75 g) were added. After 30 minutes from the first addition of initiator, the reaction mixture began to opacify indicating that the encapsulation had started. Two hours after the final addition of the initiator, the level of residual VP was checked and found to be below 500 ppm. The reaction mixture was then cooled to 50° C. and stabilizer and preservative added and dissolved therein. Then 5.67 g of a 10% sodium hydroxide solution was added. After 15 minutes under agitation. 52.5 g of SABILEZE® XL-80W* was added to thicken the mixture and, after one hour, the mixture remained stable and was transferred to a product recovery container. The bulk viscosity of the 20% product was 38,800 cps and the encapsulate size was less than 200 microns.

* stock solution of STABILEZE® QM

While the invention has been described with particular reference to certain water insoluble perfluoroethers, encapsulating polymers and thickeners, it will be understood that many modifications and substitutions can be made in accordance with the foregoing disclosure and that these variations are within the scope of this invention.

What is claimed is:

1. A stable composition comprising an aqueous suspension of water insoluble perfluoroether polymer microdroplets encapsulated by a water soluble vinyl lactam polymer.

2. The composition of claim 1 wherein the suspension contains between about 5 and about 50 wt. % solids.

3. The composition of claim 2 wherein the suspension contains between about 10 and about 30 wt. % solids.

4. The composition of claim 1 wherein the aqueous suspension has a bulk viscosity of from about 8,000 and about 100,000 cps.

5. The composition of claim 4 wherein the aqueous suspension has a bulk viscosity of between about 10,000 and about 70,000 cps.

6. The composition of claim 1 wherein the ratio of perfluoroether polymer to water soluble polymer can range from about 50/50 to about 95/5.

7. The composition of claim 1 which additionally contains thickener in an amount of between about 0.2 and about 2 wt. %, based on total composition.

8. The composition of claim 1 wherein said water insoluble perfluoroether polymer is a perfluorinated isopropyl alkyl ether polymer.

9. The composition of claim 1 wherein said water insoluble perfluorinated polymer is present as a mixture of a perfluoroether polymer containing isopropyl units and a silicone oil polymer.

10. The composition of claim 1 wherein said water soluble lactam polymer is a polymer containing at least 60 wt. % of N-vinyl pyrrolidone or N-vinyl caprolactam.

11. The composition of claim 1 wherein said perfluoroether polymer is

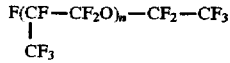

wherein n has a number average value of 4 to 15.

12. The composition of claim 1 wherein said perfluoroether polymer is

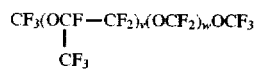

wherein the sum of v+w has a number average value of 4 to 20.

13. A personal care formulation containing an effective emolliating amount of the composition of claim 1.

14. The formulation of claim 13 which is a hair or skin care formulation.

15. The formulation of claim 14 wherein the water insoluble perfluoroether is a perfluorinated isopropyl ether.

16. A personal care, pharmaceutical or agrochemical formulation containing between about 2 and about 15 wt. % of the composition of claim 1, based on total composition.

17. A topical pharmaceutical formulation containing an effective skin or tissue conditioning and moisturizing amount of the composition of claim 1.

18. An agrochemical spray formulation containing the composition of claim 1.

19. The process of preparing the poly(perfluoroether) encapsulate of claim 1 which comprises:
   (a) adding the poly(perfluoroether) oil or oil mixture to water under agitation sufficient to form a fine dispersion of discrete oil microdroplets;
   (b) continuing agitation to produce a dispersion which is stable against phase separation for at least 5 minutes;
   (c) adding said water soluble vinyl lactam polymer and a free radical initiator to (b);
   (d) heating the resulting mixture to between about 50° and about 90° C. until the mixture opacifies within a period of from about 2 to about 20 hours and
   (e) recovering the resulting water dispersible encapsulate containing less than 1000 ppm vinyl lactam monomer.

20. The process of claim 19 wherein said initiator is oil soluble.

21. The process of claim 19 wherein said poly (perfluoroether) oil contains a silicone oil.

22. The process of claim 19 or 20 wherein said poly (perfluoroether) oil is

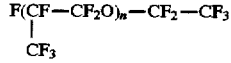

where n has a number average value of 4 to 15 or

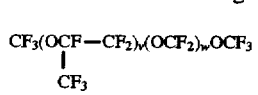

where the sum of v+w has a number average value of 4 to 20, and mixtures thereof.

23. The process of claim 19 wherein said vinyl lactam polymer is a polymer of N-vinyl pyrrolidone or N-vinyl caprolactam and mixtures thereof.

* * * * *